United States Patent [19]

Benoist

[11] Patent Number: 5,476,467
[45] Date of Patent: Dec. 19, 1995

[54] SURGICAL HAMMER FOR DRIVING K-WIRES

[76] Inventor: Louis A. Benoist, 1700 Skeels Ave., Eau Claire, Wis. 54701

[21] Appl. No.: 260,402

[22] Filed: Jun. 14, 1994

[51] Int. Cl.⁶ .......................... A61B 17/88; A61B 17/92
[52] U.S. Cl. ............................ 606/100; 606/104
[58] Field of Search ..................... 606/100, 99, 103, 606/104

[56] References Cited

U.S. PATENT DOCUMENTS 2,725,878  12/1955  Reiter ........................... 606/100
3,351,054  11/1967  Florek ........................... 606/104

FOREIGN PATENT DOCUMENTS 195429  7/1971  Germany .......................... 606/103

*Primary Examiner*—Tamara L. Graysay
*Attorney, Agent, or Firm*—Breiner & Breiner

[57] ABSTRACT

A surgical tool for driving a K-wire into bone fragment or bone with gentle but forceful precision is described. The tool provides for the driving of the K-wire with a slap hammer action while rotating the wire. The tool is of simple construction.

2 Claims, 2 Drawing Sheets

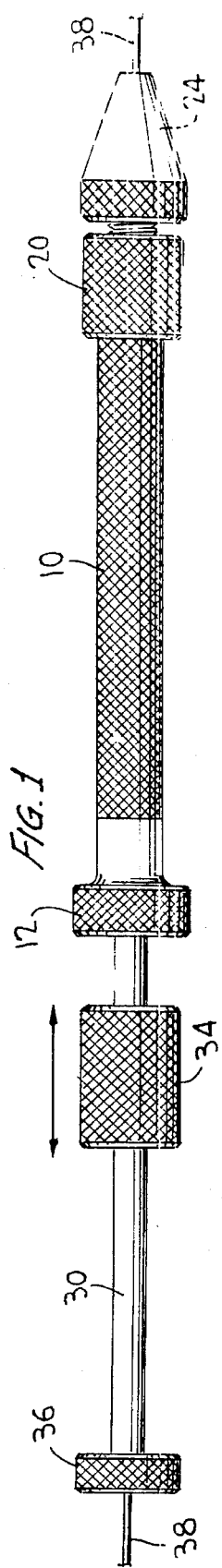
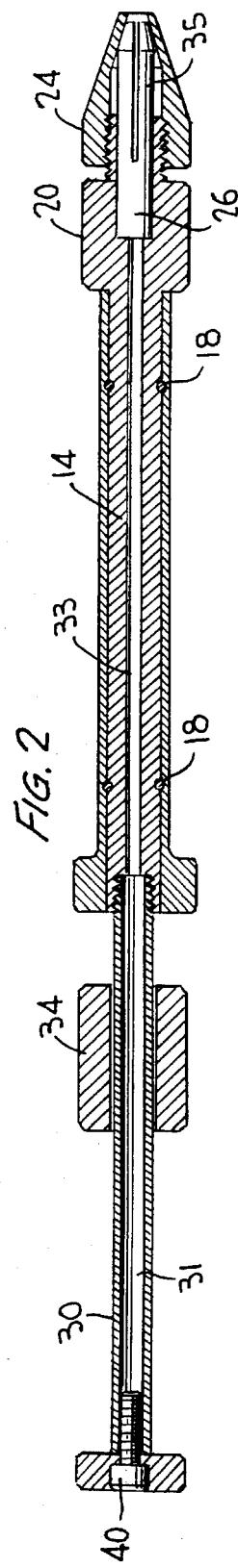
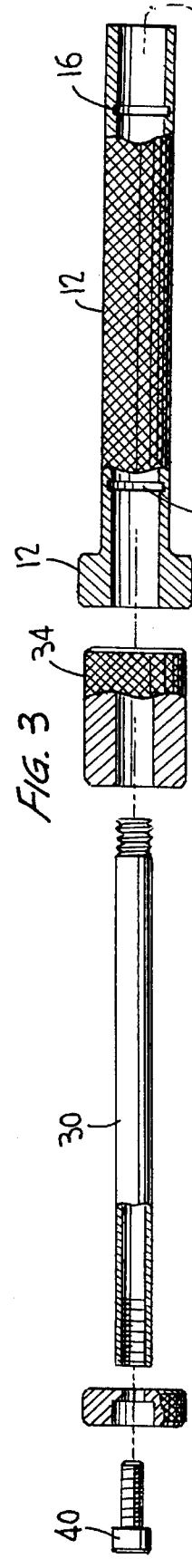
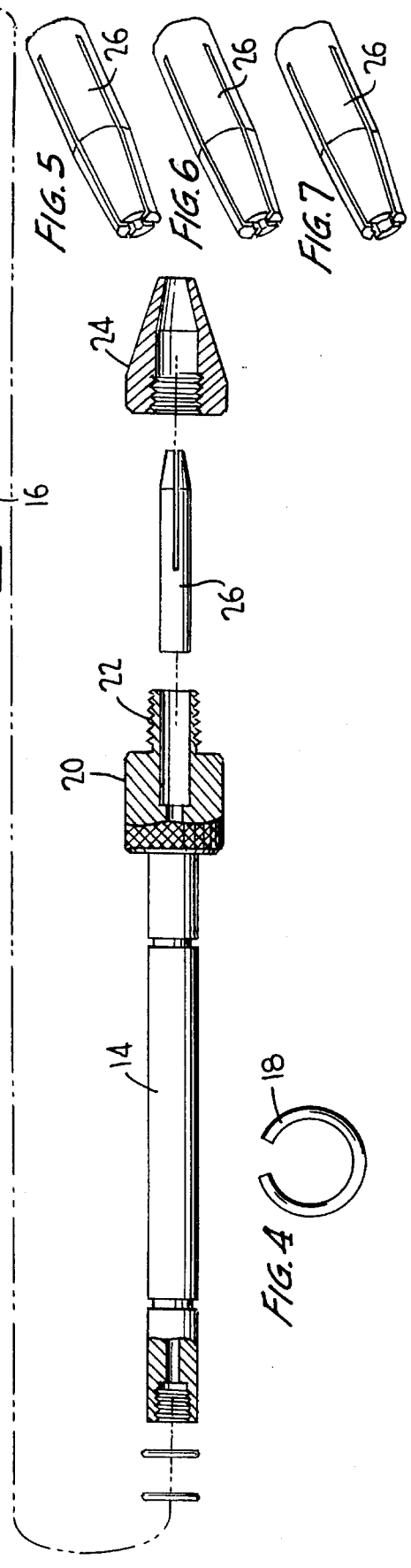

SURGICAL HAMMER FOR DRIVING K-WIRES

RELATED APPLICATION

This application is related to concurrently filed application Ser. No. 08/260,412 entitled "Device and Method for Positioning and Holding Bone Fragments in Place", now abandoned.

FIELD OF INVENTION

This invention relates to a surgical hammer for placing K-wires or the like in bone fragments. More particularly, the invention relates to a surgical hammer for the driving of a K-wire or the like into bone fragment with a hammering action with concurrent rotation of the K-wire or the like to maintain the K-wire or the like movement in a chosen direction.

BACKGROUND OF INVENTION

Devices are known for use by surgeons in various operations which can be classified as surgical mallets, hammers and the like. For example, U.S. Pat. No. 2,725,878 is directed to a surgical mallet comprising a hammer mounted for reciprocal action utilizing a compression spring for moving the hammer forward. U.S. Pat. No. 1,837,067 describes a similar device. Further, U.S. Pat. Nos. 2,200,120; 2,697,433 and 5,059,206 are directed to devices for guiding nails, wires and the like when positioning and holding bone fragments in place. U.S. Pat. No. 2,200,120 contains a detailed description of one operative procedure.

None of the surgical devices heretofore known include the ability to drive a K-wire or the like into bone fragments with gentle but forceful precision while maintaining the direction of the K-wire or the like in a chosen direction (straight or curved) when encountering the resistance of a hard bone.

OBJECTS AND SUMMARY OF INVENTION

Accordingly, it is a primary object of the present invention to provide a surgical device for driving K-wires and the like through bone fragments with precision and maintaining the direction of the wire in a chosen direction (curved or straight line).

It is another primary object of the present invention to provide a surgical device simple in construction which permits the precision driving of a K-wire or the like while simultaneously rotating the K-wire or the like to permit precision placement.

The aforesaid and other objects of the invention are accomplished by providing a surgical hammer comprising an elongated housing member or hand piece, having retained within that elongated housing member, an elongated barrel member externally threaded at a first end, and internally threaded at its second end and having an internal passageway extending from its second end to its first end for passage of a K-wire or the like. An end-tip member having internal threads, also having an internal passageway extending therethrough, is screwed onto the second end of the first elongated barrel member. The first barrel member and end-tip are constructed and arranged to house a collet again having an internal passageway for receiving a K-wire and holding the wire fast. A second barrel member preferably having an enlarged end for turning and an internal passageway is screwed into the first end of the first barrel member. A slap hammer is positioned on the second barrel member constructed and arranged to slidably ride on the second barrel member. The housing has detents at the internal surface of the housing spaced from each end for receiving a lock washer positioned around the first barrel member.

When the individual members of the device are in operable associate, a passageway for a K-wire or the like extends entirely through the device. The enclosure of the K-wire gives the operator protection from the sharp protruding end of the K-wire. The collet is chosen according to the selected diameter of the wire, i.e., a diameter of from less than 1 mm up to about 5 mm. The lock washer on the barrel member engages the detents in the internal surface of the housing, locking the two together. Accordingly, when the barrel member, or hand piece, containing the collet is rotated, all components of the device rotate within the housing or hand piece. Since the collet firmly engages the K-wire, the K-wire also rotates. When the slap hammer is slapped against the hand piece, a K-wire within the passageway is driven forward overcoming obstacles and into an object such as a bone fragment or the like.

The device provides, therefore, a relatively simple tool which permits the precision driving of a K-wire or the like into bone fragments for positioning and then holding the fragments in place while mending. It also gives the operator protection from hand punctures on the free end or proximal end of the K-wire since it is enclosed in the slap hammer end of the device.

THE DRAWING AND DETAILED DESCRIPTION

In the drawing,

FIG. 1 is a side view of the surgical wire driver of the present invention;

FIG. 2 is a sectional view of the driver shown in FIG. 1;

FIG. 3 is an exploded view, partly in section, of the driver of FIGS. 1 and 2;

FIG. 4 is a lock washer for locking the first barrel member to the interior of the housing;

FIGS. 5, 6, and 7 are of collets having passageways of varying diameter; and

Figure 8:
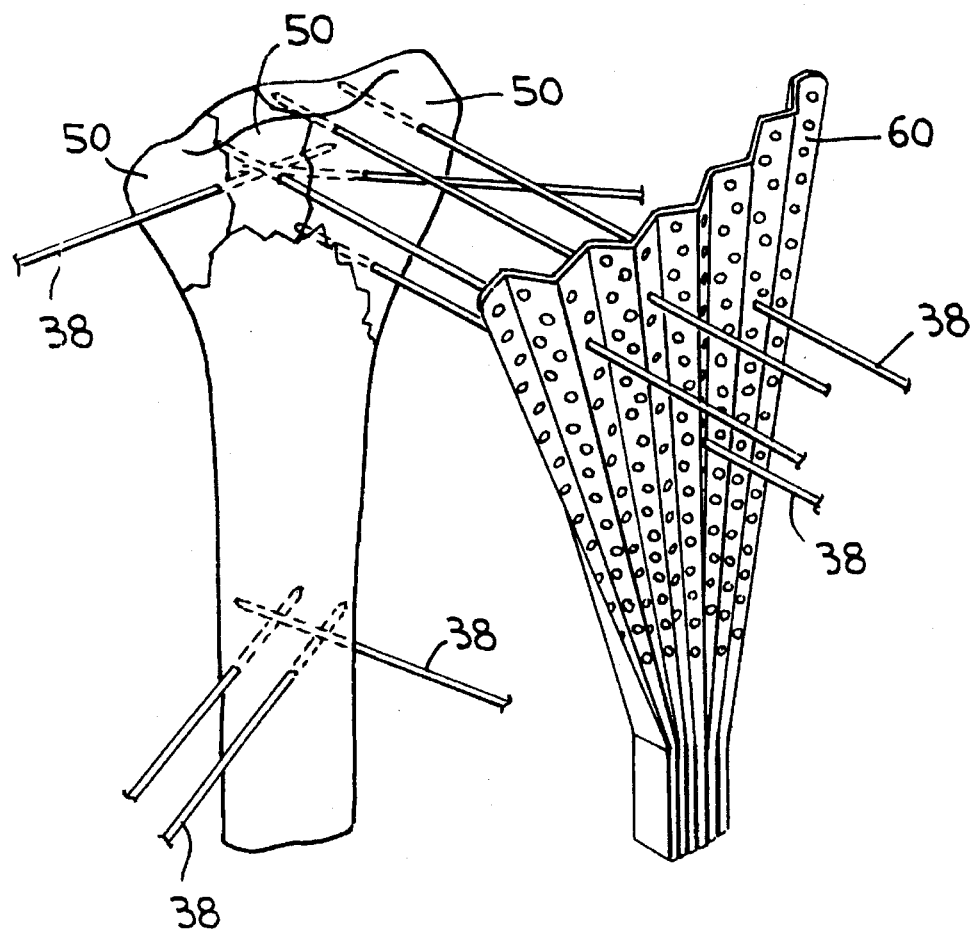
Figure 9:
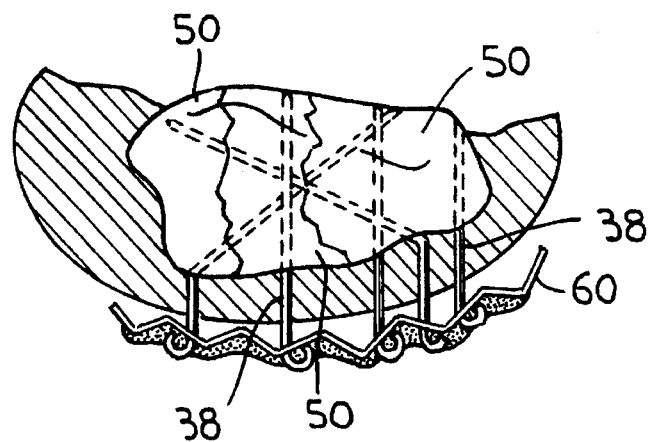

FIGS. 8 and 9 illustrate how the K-wires are placed using the driver of the present invention to position and retain bone fragments in position while mending.

Referring to the drawings, a housing 10, having an enlarged end 12, circumscribes a first barrel member 14. Barrel member 14 is locked to the interior of housing 10 through detent 16 in the interior of housing 10 which engages lock washer 18 on barrel member 14. Barrel member 14 has an enlarged end 20, leading to a threaded section 22. Enlarged end 20 and threaded section 22 are mated to a tip-end member 24, which is constructed and arranged to house a collet 26.

A second barrel member 30 is threaded to the end of first barrel member 14. A slap hammer 34 is slidably positioned over barrel member 30. Barrel member 30 has an enlarged collar 36 at its extreme end from the point of engagement with barrel member 14.

As shown in FIG. 1, a K-wire 38 can extend from one end of the surgical hammer passing through enlarged collar 36 of barrel member 30 via an internal passageway 31 which connects with passage 33 in barrel member 14 which connects with passage 35 in collet 26 and exits from tip-end 24. As shown in FIGS. 2 and 3, screw member 40 can be positioned in the end of barrel member 30 to block passageway 31. When this is done, the K-wire must be inserted into the device from tip-end 24. As shown in FIGS. 5, 6, and 7, the collet can be selected depending on the diameter of the K-wire to be utilized.

The surgical hammer can be used to drive K-wires into bone fragment 50 of a fractured bone, such as the distal end of a wrist bone as shown in FIGS. 8 and 9, to properly position the fragments. This operation, as will be appreciated, is a delicate one and must be done with precision. The surgical hammer of the present invention permits the application of a driving force, which can range from a light to a relatively heavy, as determined by the rapidity and forcefulness of the slapping of slap hammer 34. Moreover, since the K-wire can be rotated by turning the barrel member 30, which in turn will turn barrel member 14 and collet 26, the K-wire will not skew off-direction due to the resistance exerted by the bone.

As also shown in FIG. 8, the K-wire can be driven directly into the forearm bone as shown at 50. As will be appreciated, driving into the bone requires substantial force and precision guiding of a wire. The device is not designed for penetration of pure cortical bone but is excellent for guiding a K-wire up the medullary cavity of the forearm bone.

As shown in FIGS. 8 and 9, and as further disclosed in my concurrently filed application referred to above, the K-wires can be positioned in to a template member 60 having a plurality of holes for engaging the different K-wires. The K-wires after passing through the template, are bent-over and cemented to the template 60.

As will be appreciated, the surgical hammer of the present invention is relatively simple but yet permits the precise positioning and driving of a K-wire.

Although only a preferred embodiment of the surgical hammer has been specifically illustrated and described herein, it is to be understood that various modifications can be made without departing from the spirit of the invention, and the scope of the appended claims.

It is claimed:

1. A surgical tool for driving a wire into bone or bone fragments comprising a housing having an internal surface, a first barrel member having an internal passageway and having a first end and a second end; means at the internal surface of said housing to engage and retain said first barrel member and permitting rotation of said first barrel member within said housing, a tip-end member including means to secure said tip-end member to said second end of said first barrel member, said tip-end member further including means to receive a collet within said tip-end member, said collet having an internal passageway, a second barrel member secured to said first end of said first barrel member, said second barrel member having an internal passageway, a slap hammer member slideably positioned on the exterior surface of said second barrel member, said surgical tool being designed and constructed to receive a wire whereby said wire can extend through said tip-end member, into and through the passageway of said first barrel member, and into and through said second barrel member, permitting the driving of a wire forward while simultaneously rotating the wire.

2. The surgical tool of claim 1 wherein said means to permit rotation of said first barrel member within said housing is detent means at the internal surface of said housing and lock washers on said first barrel member.

\* \* \* \* \*